US008383417B2

(12) United States Patent
Lopez et al.

(10) Patent No.: US 8,383,417 B2
(45) Date of Patent: Feb. 26, 2013

(54) ASSAY FOR MONITORING PARATHYROID HORMONE (PTH) VARIANTS BY TANDEM MASS SPECTROMETRY

(75) Inventors: Mary Frances Lopez, Boston, MA (US); David A. Sarracino, Andover, MA (US); Amol Prakash, Cambridge, MA (US); Randall W. Nelson, Phoenix, AZ (US); Paul Oran, Scottsdale, AZ (US); Bryan E. Krastins, Somerville, MA (US); Taha Rezai, Cambridge, MA (US)

(73) Assignees: Thermo Finnigan, LLC, San Jose, CA (US); Intrinsic Bioprobes, Inc., Tempe, AZ (US)

( * ) Notice: Subject to any disclaimer, the term of this patent is extended or adjusted under 35 U.S.C. 154(b) by 55 days.

(21) Appl. No.: 12/644,284

(22) Filed: Dec. 22, 2009

(65) Prior Publication Data
US 2011/0151568 A1 Jun. 23, 2011

(51) Int. Cl.
*G01N 24/00* (2006.01)
*G01N 33/00* (2006.01)

(52) U.S. Cl. .............................. 436/173; 436/86; 436/89

(58) Field of Classification Search ........................ None
See application file for complete search history.

(56) References Cited

U.S. PATENT DOCUMENTS

| 6,872,575 | B2 | 3/2005 | Regnier |
| 7,348,137 | B2 | 3/2008 | Caulfield et al. |
| 2004/0072251 | A1 | 4/2004 | Anderson |
| 2005/0124010 | A1 | 6/2005 | Short et al. |
| 2006/0094125 | A1 | 5/2006 | Singh et al. |
| 2006/0228809 | A1 | 10/2006 | Clarke et al. |
| 2009/0090856 | A1 | 4/2009 | Grant et al. |

OTHER PUBLICATIONS

Lange et al., "Selected reaction monitoring for quantitative proteomics: a tutorial", Molecular Systems Biology, 2008, v. 4, article No. 222, pp. 1-14.*
Lopez et al., "Selected Reaction Monitoring-Mass Spectrometric Immunoassay Responsive to Human Parathyroid Hormone and Related Variants," Clinical Chemistry, vol. 56 (2009), pp. 281-290.
Nedelkov et al., "Investigating Diversity in Human Plasma Proteins," PNAS Aug. 2, 2005, 102 (31), pp. 10852-10857.
Zhang et al., "Identification of Carboxyl-Terminal Peptide Fragments of Parathyroid Hormone in Human Plasma at Low-Picomolar Levels by Mass Spectrometry," Anal. Chem., 2006, 78 (5), pp. 1636-1643.
Martin et al., "The Vagaries of the Parathyroid Hormone Assay," Sep. 27, 2007, pp. 1-2, http://cme.medscape.com/viewarticle/558652.
Niederkofler et al., "Detection of Endogenous B-Type Natriuretic Peptide at Very Low Concentrations in Patients with Heart Failure," Circulation Heart Failure, 2008 (1), pp. 258-264.

(Continued)

*Primary Examiner* — Yelena G Gakh
(74) *Attorney, Agent, or Firm* — Charles B. Katz

(57) ABSTRACT

Methods are described for monitoring the amounts of PTH variants in a biological sample by digesting the sample to produce surrogate peptides specific to the targeted PTH variants, and detecting and quantifying the surrogate peptides by selective reaction monitoring (SRM) mass spectrometry, using a set of precursor-to-product ion transitions optimized for sensitivity and selectivity. The PTH variants, or a portion thereof, may be concentrated in the sample by means of immunoaffinity capture or other suitable technique. The mass spectrometric method described herein enables the concurrent measurement of peptides representative of a plurality of targeted PTH variants in a single assay.

9 Claims, 9 Drawing Sheets

OTHER PUBLICATIONS

Lopez et al., "Design of a Selected Reaction Monitoring Mass Spectrometric Immunoassay Responsive to Human Parathyroid Hormone and Related Variants," Clinical Chemistry Manuscript No. CLINCHEM/2009/137323, pp. 1-26.

* cited by examiner

SEQUENCE LISTING

<160> NUMBER OF SEQ ID NOS: 8

<210> SEQ ID NO 1
<211> LENGTH: 7
<212> TYPE: PRT
<213> ORGANISM: Homo sapiens

<400> SEQUENCE: 1

His Leu Asn Ser Met Glu Arg
1               5

```
<210> SEQ ID NO 2
<211> LENGTH: 7
<212> TYPE: PRT
<213> ORGANISM: Homo sapiens

<400> SEQUENCE: 2

Gly Ala Pro Leu Ala Pro Arg
1               5

<210> SEQ ID NO 3
<211> LENGTH: 7
<212> TYPE: PRT
<213> ORGANISM: Homo sapiens

<400> SEQUENCE: 3

Leu Met His Asn Leu Gly Lys
1               5

<210> SEQ ID NO 4
<211> LENGTH: 8
<212> TYPE: PRT
<213> ORGANISM: Homo sapiens

<400> SEQUENCE: 4

Leu Gly Ala Pro Leu Ala Pro Arg
1               5

<210> SEQ ID NO 5
<211> LENGTH: 8
<212> TYPE: PRT
<213> ORGANISM: Homo sapiens

<400> SEQUENCE: 5

Ala Asp Val Asn Val Leu Thr Lys
1               5

<210> SEQ ID NO 6
<211> LENGTH: 11
<212> TYPE: PRT
<213> ORGANISM: Homo sapiens

<400> SEQUENCE: 6

Phe Val Ala Leu Gly Ala Pro Leu Ala Pro Arg
1               5                   10

<210> SEQ ID NO 7
<211> LENGTH: 13
<212> TYPE: PRT
<213> ORGANISM: Homo sapiens

<400> SEQUENCE: 7

Ser Val Ser Glu Ile Gln Leu Met His Asn Leu Gly Lys
1               5                   10

<210> SEQ ID NO 8
<211> LENGTH: 17
<212> TYPE: PRT
<213> ORGANISM: Homo sapiens

<400> SEQUENCE: 8

Leu Gln Asp Val His Asn Phe Val Ala Leu Gly Ala Pro Leu Ala Pro
1               5                   10                  15

Arg
```

ASSAY FOR MONITORING PARATHYROID HORMONE (PTH) VARIANTS BY TANDEM MASS SPECTROMETRY

FIELD OF THE INVENTION

The present invention relates generally to monitoring parathyroid hormone (PTH) in biological samples, and more particularly to a tandem mass spectrometry-based method for concurrently measuring peptides characteristic of two or more PTH variants.

BACKGROUND OF THE INVENTION

Parathyroid hormone (PTH) is produced in the parathyroid glands through the two-step conversion of pre-pro-PTH (115-amino acids) to pro-PTH (90-amino acids) to the 84-amino acid peptide PTH(1-84). The hormone is secreted into the circulatory system to produce basal (healthy) concentrations of ~15-65 pg/mL, and is assayed to assist in the diagnosis of hypo/hyperparathyroidism, hypercalcemia and in monitoring for renal osteodystrophy in patients with end-stage renal failure. Conventional PTH assays typically rely on two-antibody recognition systems coupled to a variety of detection modalities (e.g., enzymatic amplification, electrochemiluminescence, and fluorescence). Notably, assays of greatest specificity are able to differentiate between different truncated forms of PTH, and are referred to as "second" or "third" generation PTH assays.

Of particular importance to these later-generation assays is their ability to selectively monitor different PTH forms of known biological consequence. Notably, two variants, full-length PTH(1-84) and PTH missing the six N-terminal amino acids (PTH(7-84)), are the subject of increased clinical investigation and potential diagnostic capability. Due to confounding microheterogeneity, these variants were historically considered as a single PTH value (i.e., by the "first" generation assays). Classification of each as its own molecular entity, and the ability to analyze and study each independently, suggests an antagonistic relationship between the two different forms in relationship to calcium homeostasis. As such, there is mounting clinical evidence that the ratio between PTH(1-84) and PTH(7-84) may differentiate between hyperparathyroid bone turnover and adynamic bone disease.

This PTH(1-84)-to-PTH(7-84) paradigm is a most recent example of describing the biological and clinical utility of microheterogeneity within the PTH protein. Indeed, other PTH variants have been defined as far back as ~40 years ago. Perhaps the most mature of these, PTH(1-34), has been identified as an endogenous variant that exhibits biochemical activity comparable to the full-length protein. Consequently, it represents a classic example of a peptide-based bioactive variant that has transitioned through drug development to the point of FDA-approval for the treatment of osteoporosis (rPTH(1-34) (teriparatide)). Collectively the routine monitoring of these clinically-relevant PTH variants—PTH(1-84), PTH(7-84) and PTH(1-34)—is achieved through three separate, high-specificity immunometric assays. However, there are indications that even greater microheterogeneity exists within PTH, which has yet to be fully characterized to determine clinical utility and/or confounding effects on present-day assays. The accurate examination of known PTH variants, while simultaneously evaluating other possible variants, requires a degree of analytical freedom of which conventional assays are generally incapable.

SUMMARY

Roughly described, the present invention provides methods for concurrent monitoring of a plurality of PTH variants of interest by selective reaction monitoring (SRM) tandem mass spectrometry. According to one illustrative embodiment, a biological sample, such as blood serum or plasma, is prepared for analysis by proteolytically (e.g., tryptically) digesting the sample to yield peptide fragments, certain ones of which are specific to a particular PTH variant (referred to herein as surrogate peptides). Immunoaffinity capture may be employed either prior to or following digestion as a means for concentrating the PTH or peptide fragments derived therefrom. The prepared sample, containing the surrogate peptides, is separated and purified by liquid chromatography (LC) or other suitable technique and subsequently introduced into a tandem mass spectrometer, for example a triple quadrupole mass spectrometer, capable of monitoring multiple transitions in SRM mode. By selection of an appropriate set of precursor-to-product ion transitions corresponding to ions produced by ionizations of the surrogate peptides, the amounts of two or more surrogate peptides present in the sample may be determined concurrently with high sensitivity and specificity.

In a specific implementation, the PTH variants of interest include PTH(1-84), otherwise referred to as intact PTH, and one or more truncated forms of PTH, such as PTH(34-84) and PTH(7-84). To monitor PTH(1-84), the mass spectrometer is operated to measure mass spectral peaks appearing at least two precursor-to-product ion transitions corresponding to the SEQ ID NO: 7 peptide, which may include m/z 486→636 and 486→684. To monitor PTH(34-84), the mass spectrometer is operated to measure peaks appearing at least two precursor-to-product ion transitions corresponding to the SEQ ID NO: 6 peptide, which may include m/z 556→343, 556→456, 556→553, 556→624, 556→681, 556→794 and 556→865. Finally, to monitor PTH(7-84), the mass spectrometer is operated to measure signals appearing at least two precursor-to-product ion transitions corresponding to the SEQ ID NO: 3 peptide, which may include 407→317, 407→431, and 407→568.

DETAILED DESCRIPTION OF EMBODIMENTS

Figure 1:
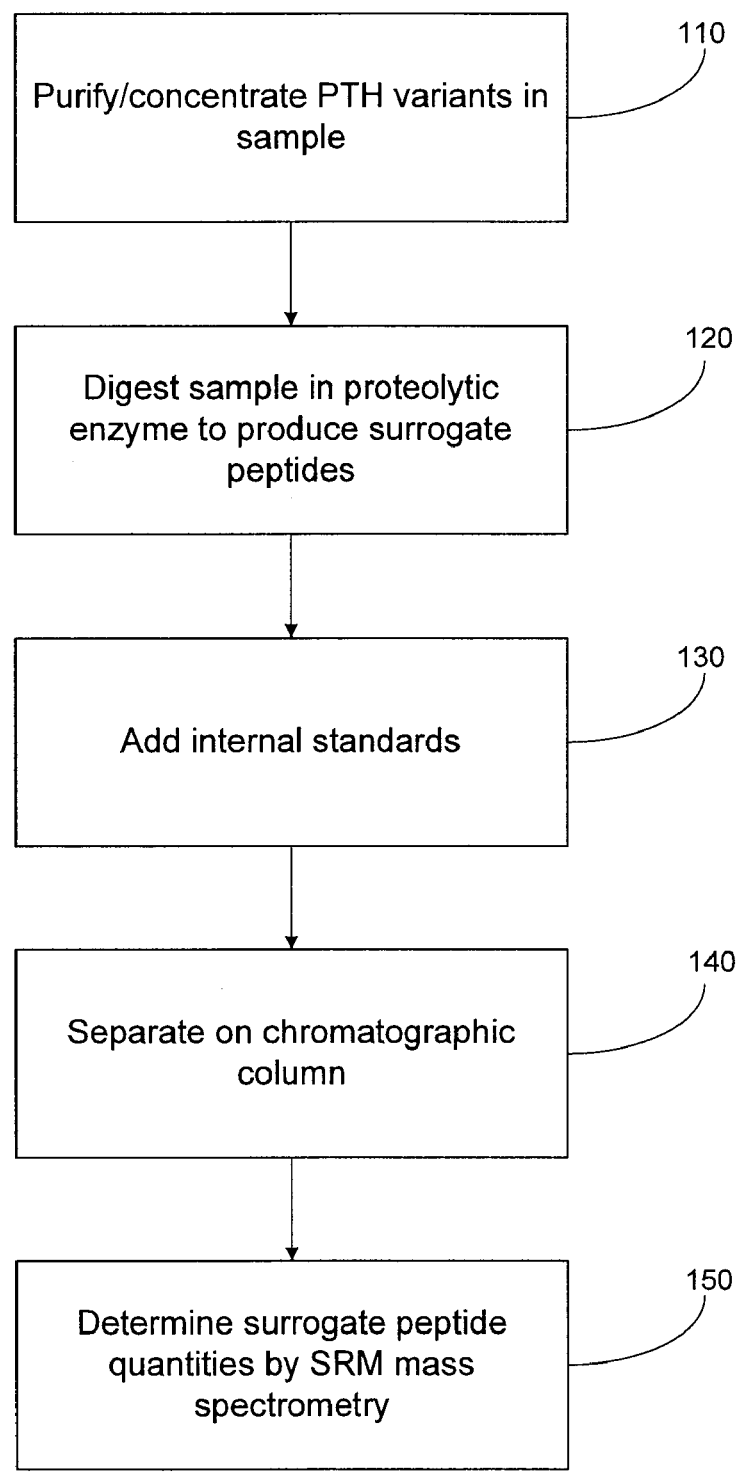
FIG. 1 is a flowchart depicting steps of a method for concurrently monitoring a plurality of PTH variants present in a biological sample.

FIG. 1 is a flowchart depicting a method for monitoring PTH variants in a biological sample, in accordance with an illustrative embodiment of the present invention. In general, the method includes steps for preparing a biological sample, and then conducting selective reaction monitoring (SRM) mass spectrometric analysis on the prepared sample to detect and quantify precursor/product ion pairs formed from surrogate peptides, with each surrogate peptide being specific to a corresponding PTH variant. As used herein, the term "PTH variant" embraces intact PTH as well as any endogenously modified forms of PTH, including forms truncated at the N-terminus and/or C-terminus. The biological sample will preferably take the form of blood serum or plasma, although alternative implementations of the present assay may test other biological fluids or tissue extracts.

In step 110, the PTH present in the biological sample is purified and concentrated to remove potentially interfering species and improve the overall limits of detection and quantitation. Purification and concentration of the PTH may be accomplished by utilization of immunoaffinity capture, the pertinent details of which are discussed in the example set forth below. As is known in the art, immunoaffinity capture entails exposing the sample to antibody binding agents immobilized on a support, such that a targeted protein present in the sample are selectively captured by the binding agents. The targeted proteins are subsequently released from the support by elution with a small volume of solvent. In the present example, a single, high-affinity polyclonal antibody is employed to simultaneously capture PTH variants having a conserved C-terminus. Other implementations of the assay may utilize a different binding agent to extract PTH variants having a truncated C-terminus. It should be understood that the scope of the present invention should not be construed as being limited to methods that utilize immunoaffinity capture, and that other protein purification/concentration techniques known in the art may be employed in addition to or in place of immunoaffinity capture.

In step 120, the purified sample is proteolytically (e.g., tryptically) digested to produce peptide fragments. A portion of the proteolytic peptide fragments (also referred to herein as PTH peptides) will be specific to corresponding PTH variants, and thus may be employed as surrogate peptides for monitoring the quantities of the corresponding PTH variants by mass spectrometry. In the example discussed below, the sample is digested by the addition of trypsin, and three targeted PTH variants are monitored by mass spectrometry: PTH(1-84) (intact PTH) and two N-terminally truncated forms, PTH(7-84) and PTH(34-84). The tryptic fragment SEQ ID NO: 7, constituting the first to thirteenth amino acid of the full PTH sequence (aa1-13), is specific to PTH(1-84) and serves as its surrogate peptide. The tryptic fragments SEQ ID NO: 3 (aa7-13) and SEQ ID NO: 6 (aa34-44) are specific to PTH(7-84) and PTH(34-84), respectively, and serve as their surrogate peptides.

It will be recognized by those skilled in the art that a surrogate peptide does not have to uniquely correspond to (i.e., be solely derived from) a single PTH variant, but need only be specific to one PTH variant of the group of targeted PTH variants monitored in a mass spectrometric assay. For example, the tryptic fragment SEQ ID NO: 7 may be produced by PTH variants other than PTH(1-84), specifically those variants having a conserved N-terminus, but is not produced by the other targeted PTH variants PTH(7-84) and PTH(34-84), and hence SEQ ID NO: 7 may serve as a surrogate for PTH(1-84) in the example described above.

According to an alternative embodiment of the assay, the biological sample may first be proteolytically digested, followed by concentration of at least the surrogate peptides. If the immunoaffinity capture technique is employed for purification, then capture antibodies for each of the purified peptide fragments will need to be identified or developed, since peptide fragments present in the digest that are not captured will not be detectable in the mass spectrometric analysis.

To facilitate accurate quantitation of the surrogate peptides by mass spectrometry, a set of isotopically-labeled synthetic versions of the surrogate peptides may be added in known amounts to the sample for use as internal standards, step 130. Since the isotopically-labeled peptides have physical and chemical properties substantially identical to the corresponding surrogate peptide, they co-elute from the chromatographic column and are easily identifiable on the resultant mass spectrum. In other implementations of the invention, labeled peptides may be added to the sample prior to the purification and/or digestion steps.

Next, the purified and digested sample containing the surrogate peptides (and associated internal standards) is chromatographically separated by using a suitable HPLC column and elution protocol in order to temporally isolate different compounds in the prepared sample and simplify the process of identifying and quantifying substances in the mass spectra, step 140. In a preferred mode of the invention, chromatographic separation is performed on-line, such that the column eluate is directly introduced into the inlet of the ion source of the mass spectrometer, for example through an electrospray ionization probe. Alternatively, fractions of the eluate may be collected and stored for later mass analysis. Other suitable separation techniques known in the art, such as electrophoresis, may be utilized in place of or in addition to HPLC.

In step 150, the prepared sample is ionized, for example by electrospray ionization, and the resultant ions are analyzed by mass spectrometry to detect and quantify two or more surrogate peptides present in the sample. Mass spectrometric analysis of the prepared sample may be carried out in any instrument capable of monitoring multiple transitions in SRM mode. In a preferred implementation, the prepared sample is analyzed in a triple quadrupole mass spectrometer, such as the Thermo Scientific Vantage TSQ instrument. Triple quadrupole mass spectrometers utilize two resolving quadrupoles, also referred to as quadrupole mass filters, each of which is operable to selectively transmit only ions having a mass-to-charge ratio (m/z) of interest. An RF-only quadrupole filled with a collision gas (a collision cell) is interposed in the ion path between the two resolving quadrupoles. Precursor ions selected in the first resolving quadrupole undergo energetic collisions in the collision cell to yield fragment ions. The fragment ions pass into the second resolving quadrupole, and the selectively transmitted product ions strike a detector, which generates a signal representative of the quantity of transmitted ions. A specified pair of precursor/product ion m/z's to which the first and second resolving quadrupoles are tuned is referred to as a transition. The instrument controller, which controls the RF and resolving DC voltages individually applied to the first and second resolving quadrupoles, is configured to rapidly cycle among individual transitions in a stored list such that a large number of different transitions may be concurrently monitored. The number of transitions that may be concurrently monitored in a given time period will depend on various operational factors, including the settling time of the resolving quadrupoles and the rate at which product ions are removed from the collision cell; commercially available instruments are typically capable of monitoring a few hundred transitions per second.

Due to the multiplicity of charge states and fragmentation that exist for each peptide fragment, monitoring all possible precursor-to-product ion transitions for the group of surrogate peptides is generally impractical. Instead, the mass spectrometer is operated to monitor a subset of transitions selected to optimize sensitivity and selectivity for each surrogate peptide. In a typical assay, a set of 4-8 transitions are monitored for each targeted peptide fragment, comprising 2-4 transitions for the wild-type peptide (i.e., the peptide fragment derived from digestion of the PTH variant in the sample) and an equivalent number of transition for the corresponding isotopically-labeled synthetic peptide. The selection of optimized transitions for particular surrogate peptides may be performed in an automated or semi-automated fashion using Thermo Scientific Pinpoint software, which identifies and refines an optimized set of transitions based on the expected transition intensity (determined using fragmentation rules and/or previously acquired data) and potential interferences (arising for example, from co-eluting peptide fragments derived from the sample matrix or other surrogate peptide fragments). The process of optimizing a set of transitions for a targeted peptide fragment is discussed in greater detail in U.S. patent application Ser. No. 12/163,928 for "Optimizing Selection of SRM Transitions for Analysis of Biomolecules by Tandem Mass Spectrometry", the disclosure of which is incorporated herein by reference.

The following sets of transitions have been found to provide high degrees of sensitivity and selectivity for detection/quantitation of the associated surrogate peptides. The peptide SEQ ID NO: 7, which is specific to the PTH(1-84) variant, may be identified by operating the mass spectrometer to detect ions at the following transitions: m/z 486→636 and 486→684. The peptide SEQ ID NO: 6, which is specific to the PTH(34-84) variant, 556→343, 556→456, 556→553, 556→624, 556→681, 556→794 and 556→866. Finally, the peptide SEQ ID NO: 3, which is specific to the PTH(7-84) variant, may be identified by operating the mass spectrometer to detect ions at the following transitions: 407→317, 407→431, and 407→568. It will be recognized that the m/z values specified above are nominal (rounded integer) values and are therefore approximate, and that the preferred embodiments of the invention include the use of transitions that have precursor/product ion m/z's that are within ±0.5 of the foregoing values. Examples of more precise transition values are listed in the appended tables, which are discussed below. Alternative implementations of the assay may use a greater or lesser number of transitions for each surrogate peptide; however, it is generally advisable to use at least two transitions for each peptide to ensure an acceptable degree of specificity and avoid misidentification of targeted substances. It will be further recognized that when isotopically-labeled synthetic peptides are employed as internal standards, the isotopically-labeled peptides may be identified by monitoring a set of transitions that correspond to those used for identification of the associated surrogate peptide, adjusted for the increased or decreased mass arising from the isotope labels.

Various data acquisition strategies have been developed and have been implemented in control software for increasing instrument efficiency by avoiding the need to monitor all of the specified transitions at all time. These strategies, which have been referred to as "intelligent SRM", may involve time-scheduled monitoring of primary transitions corresponding to molecules of interest based on expected elution times, as well as data-dependent monitoring of secondary transitions of the molecules of interest (to provide greater specificity) triggered by detecting intensities at the primary transitions that exceed a threshold. Utilization of intelligent SRM techniques may be particularly advantageous in implementations where a large number of PTH variants are monitored, or where the analyzed sample contains a complex mixture of PTH-derived peptides and components produced by digestion of compounds in the sample matrix.

Once the mass spectrometric analysis of the prepared sample has been completed, the quantities of the surrogate peptides in the sample may be determined by integration of the relevant peak areas, as known in the prior art. When isotopically-labeled internal standards are used, as described above, the quantities of the surrogate peptides of interest are established via an empirically-derived or predicted relationship between surrogate peptide quantity (which may be expressed as concentration) and the area ratio of the surrogate peptide and internal standard peaks at specified transitions. Other implementations of the assay may utilize external standards or other expedients for peptide quantification. The absolute or relative quantities of the surrogate peptides, representative of the respective PTH variants from which they are formed, may provide useful information for a variety of clinical purposes, including (without limitation), the diagnosis of renal or skeletal diseases, and monitoring the effectiveness of treatments for such diseases.

It will be appreciated that the SRM mass spectrometry technique practiced in accordance with the present invention enables the concurrent monitoring of a plurality of PTH variants in a biological sample, via detection and quantitation of their corresponding surrogate peptides. The term "concurrent", as used herein, does not denote or require simultaneous or near-simultaneous detection of the different surrogate peptides, but instead denotes that the two or more surrogate peptides may be measured in a single assay, e.g., within a single chromatographic run. This approach stands in contradistinction to immunoassays and other prior art techniques, in which separate variant-specific assays need to be conducted to monitor selected PTH variants.

A detailed example of an implementation of the PTH assay of the invention is set forth below. The following example is intended to illustrate rather than limit the scope of the present invention. In particular, the specific PTH variants discussed above and in the following example represent a small subset of possible PTH variants, and the SRM mass spectrometry technique of the invention should not be construed as being limited to the disclosed PTH variants. Those skilled in the art will recognize that there are thousands of possible PTH variants that arise from truncation from intact PTH(1-84), and that this number is expanded exponentially when post-translation modifications of the truncated PTH variants are considered. The technique of the present invention, in which SRM mass spectrometry is employed to concurrently determine the amounts of surrogate peptides derived from two or more PTH variants, may be advantageously utilized in connection with any combination of the possible PTH variants for which monitoring is desired.

EXAMPLE

Reagents

Goat polyclonal Anti PTH39-84 antibody was purchased from Immutopics International (San Clemente, Calif.). Recombinant human PTH (rhPTH) was obtained from Bachem (Torrance, Calif.). Premixed MES-buffered saline powder packets were from Pierce (Rockford, Ill.). Extraction of PTH from plasma was carried out with proprietary MSIA pipette tips (MSIA-Tips) from Intrinsic Bioprobes (Tempe, Ariz.) derivatized with the PTH antibodies via 1,1' carbonyldiimidazole (CDI) chemistry as described below. Premade 10×0.1M Hepes-buffered saline (HBS-N) with 30 mM EDTA and 0.2% (v/v) surfactant P20 (HBS-EP) was purchased from BIACORE (Piscataway, N.J.). Synthetic heavy labeled peptides were obtained from Thermo Fisher Scientific (Ulm, Germany). All other chemicals were obtained from Sigma-Aldrich (St. Louis, Mo.).

Samples

All samples used in this study were acquired under Institutional Review Board (IRB) approved protocols and with informed consent. Twenty four serum samples representing twelve clinically diagnosed individuals with renal failure (10 males and 2 female; mean age 66.7) and twelve healthy individuals (10 males and 2 female; mean age 65) were used in the population study. Standard curves were prepared in pooled human plasma by step-wise, 2-fold serial dilution from an initial sample containing rhPTH at a concentration of 150 pg/mL (7-steps: range; 150 pg/mL to 1.2 pg/mL).

Sample Preparation and Immunocapture

MSIA-Tips were provided by Intrinsic Bioprobes pre-exposed to 15 kDa carboxymethyldextran and CDI creating a highly functionalized carboxylic acid surface, as previously described in Niederkofler et al., *Novel mass spectrometric immunoassays for the rapid structural characterization of plasma apolipoproteins*, J. Lipid Res. 44:3, 630-9 (2003), the contents of which are incorporated herein by reference. The MSIA-Tips were rinsed with 0.2 M hydrochloric acid and acetone to generate free acid carboxyl groups by washing off any remaining sodium/potassium salts. MSIA-tips were subsequently activated with CDI in 1-methyl-2-pyrrolidone (NMP) by continuously pipetting the solution up and down (150 µL/well; 50 µL vol; 450 cycles) with a Beckman Multimek 96 pipetting robot (Beckman Coulter, Fullerton, Calif., USA). Tips were then blotted to remove excess NMP, rinsed twice with NMP (400 µL/well; 100 µL vol; 10 cycles), and finally blotted once more to remove any remaining excess NMP. While still slightly moist with NMP, MSIA-Tips were then immediately exposed to anti-PTH antibodies in MES buffered saline, pH 4.7 (0.25 g/L; 30 µL/well; 10 µL volume; 50 cycles; 15 repetitions/loops, approximately 45 minute exposure time) to facilitate covalent attachment to the MSIA-Tips. Finally, MSIA-Tips were rinsed with 1M ethanolamine, pH 8.5 (400 µL/well; 100 µL vol; 50 cycles) to quench any remaining CDI-preactivated sites, followed by two rinses of BBS-N (400 µL/well; 100 µL vol; 50 cycles). MSIA-Tips were stored in HBS-N at 4° C. and used within one-week of preparation. For all samples in this study, one milliliter of human serum (or plasma) was diluted with 750 µL HBSEP to result in a total analytical volume of 1.75 mL. PTH was then extracted with the aid of a Beckman Multimek 96 pipetting robot by repeatedly (1,500 repetitions) drawing and expelling (back into the analytical volume) 125 µL aliquots of the analytical volume through the antibody prelinked MSIA-Tip. After extraction, the pipettes were rinsed using HBS-EP and H2O, (in this order, each rinse=15 repetitions of 150 µL), after which PTH was analyzed using MRM mass spectrometry as described below.

Sample Elution and Trypsin Digestion

Bound proteins were eluted from the tips into a 96 well plate (Abgene, AB-1300) by pipetting 100 of 30% acetonitrile/0.5% formic acid up and down for a total of 15 cycles. Samples were lyophilized to dryness, resuspended in 30 µL of 30% n-propanol/100 mM ammonium bicarbonate pH 8.0, diluted with 100 µL of 25 mM acetic acid containing 100 ng of trypsin. Samples were allowed to digest for 4 hours at 37° C. Post digestion, samples were lyophilized and resuspended in 30 µL of 3% (v/v) acetonitrile/0.2% (v/v) formic acid/glucagon/PTH heavy peptides.

Multiple Reaction Monitoring Assays

SRM assays were developed on a Thermo Scientific TSQ Vantage triple quadrupole mass spectrometer, Accela pump, CTC PAL Autosampler and an IonMax electrospray ionization source equipped with a high flow metal needle (Thermo Fisher Scientific). Reverse phase separations were carried out on a 1 mm×100 mm Hypersil Gold 1.9 µm C18 particle column (Thermo Fisher Scientific). Solvent A was LC-MS grade water with 0.2% (v/v) formic acid, and solvent B was LC-MS grade 30% (v/v) acetonitrile with 0.2% (v/v) formic acid (Optima grade reagents, Thermo Fisher Scientific). Pinpoint software (Thermo Fisher Scientific) was used for targeted protein quantitation. The recently developed software algorithm automates the prediction of candidate peptides and the choice of multiple fragment ions for SRM assay design. In addition, Pinpoint creates the instrument method and sequence file, and automates peptide identity confirmation and quantitative data processing. For the workflow described herein, the intact PTH sequence was imported into Pinpoint, digested with trypsin in silico, and transitions for each peptide were predicted using the batch option in the software. This initial list of peptides and transitions (which are presented in the appended Table I) was tested with recombinant PTH digest to determine those peptides and transitions delivering optimal signal. After several iterations, a subset of 6 peptides, including 2 peptides specific for the truncated variants PTH (7-84) and PTH(34-84), were chosen, along with multiple corresponding transitions. Table II lists the targeted peptides and associated transitions selected for the assay. Further assays were conducted with this optimized method. Once the target peptides were identified, synthetic heavy versions were synthesized (Thermo Fisher Scientific, Ulm, Germany) to be used as internal quantitative standards.

Target peptides were subsequently identified and quantified by co-eluting light and heavy-labeled transitions in the chromatographic separation. Time alignment and relative quantification of the transitions was performed with Pinpoint. All samples were assayed in triplicate.

Generation of Standard Profile and Evaluation Using Intact PTH

Figure 2:
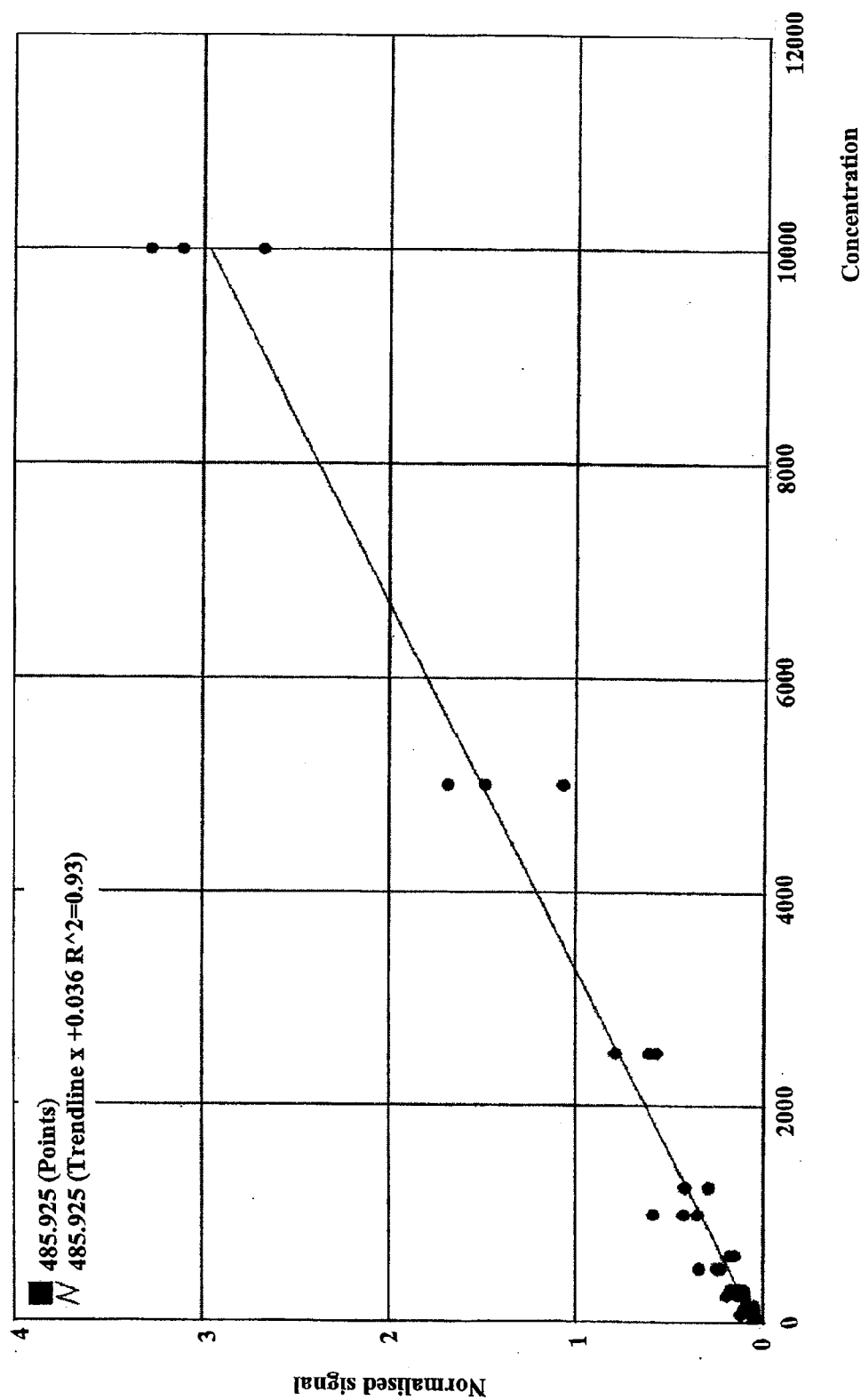
FIG. 2 is a graph showing the linear variation in peak intensity with increasing PTH concentration for transitions characteristic of the SEQ ID NO: 7 surrogate peptide.

Standard curves were created for all target tryptic peptides through serial dilution using recombinant human PTH (rhPTH) spiked into stock human blood plasma. As illustrated in the FIG. 2 example for peptide SEQ ID NO: 7 (specific to PTH(1-84)), SRM transitions exhibited linear responses (with an $R^2$ value of about 0.93) relative to rhPTH concentration, with a limit of detection for intact PTH of approximately 8 pg/ml. The standard error of analysis for triplicate measurements ranged from 3-12% for all peptides with less than <5% chromatographic drift between replicates, indicating high accuracy and reproducibility between measurements. Monitoring of variant SRM transitions showed no inflections relative to rhPTH concentration, as may be expected due to the absence of truncated variants in the stock rhPTH.

Evaluation of Clinical Samples Using Standard Profile and Variant Transitions.

Figure 3A:
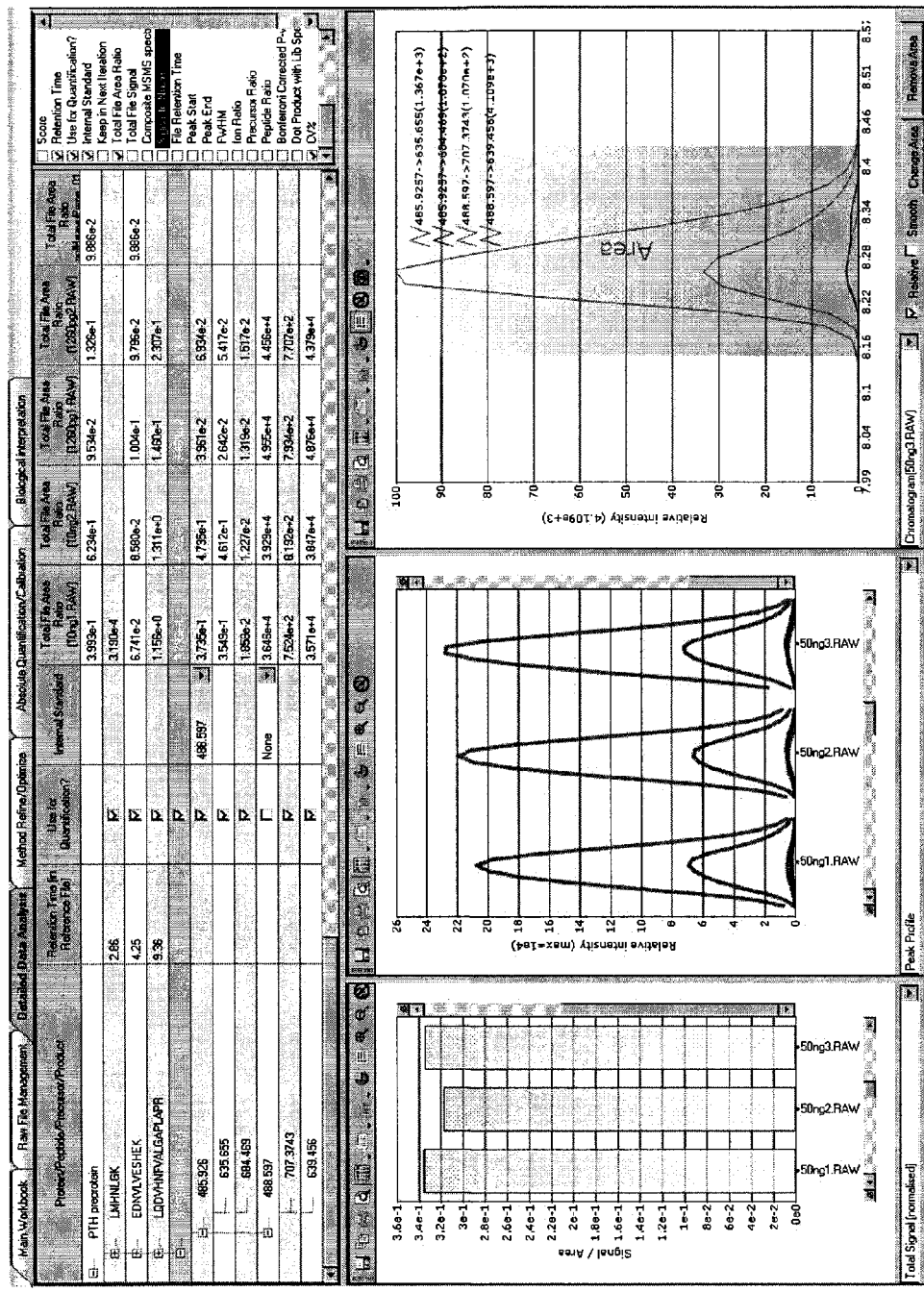
FIGS. 3A and 3B are screen captures of mass spectrometry data acquired for two surrogate peptides: SEQ ID NO: 7 and SEQ ID NO: 3.
Figure 3B:
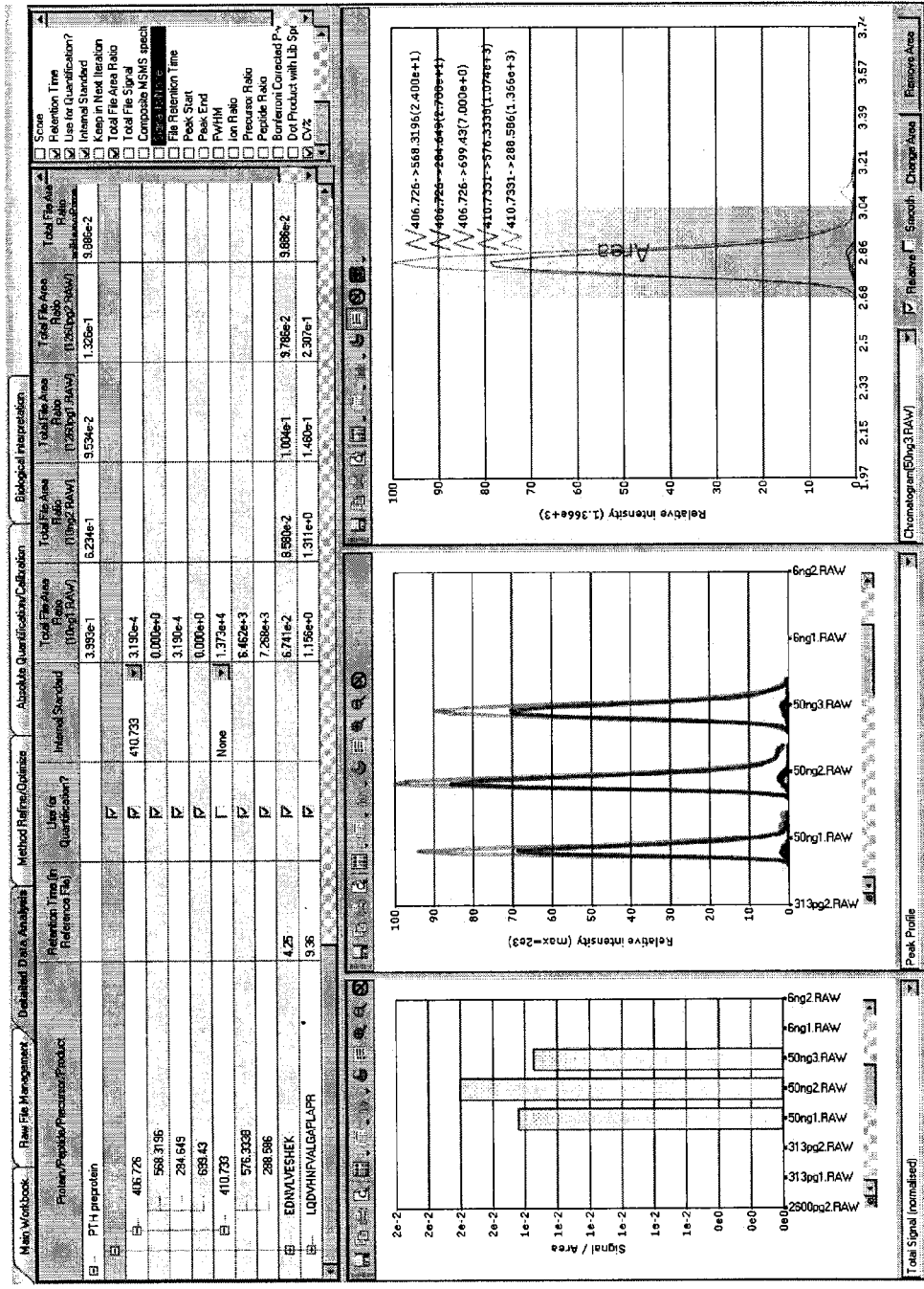
Figure 4A:
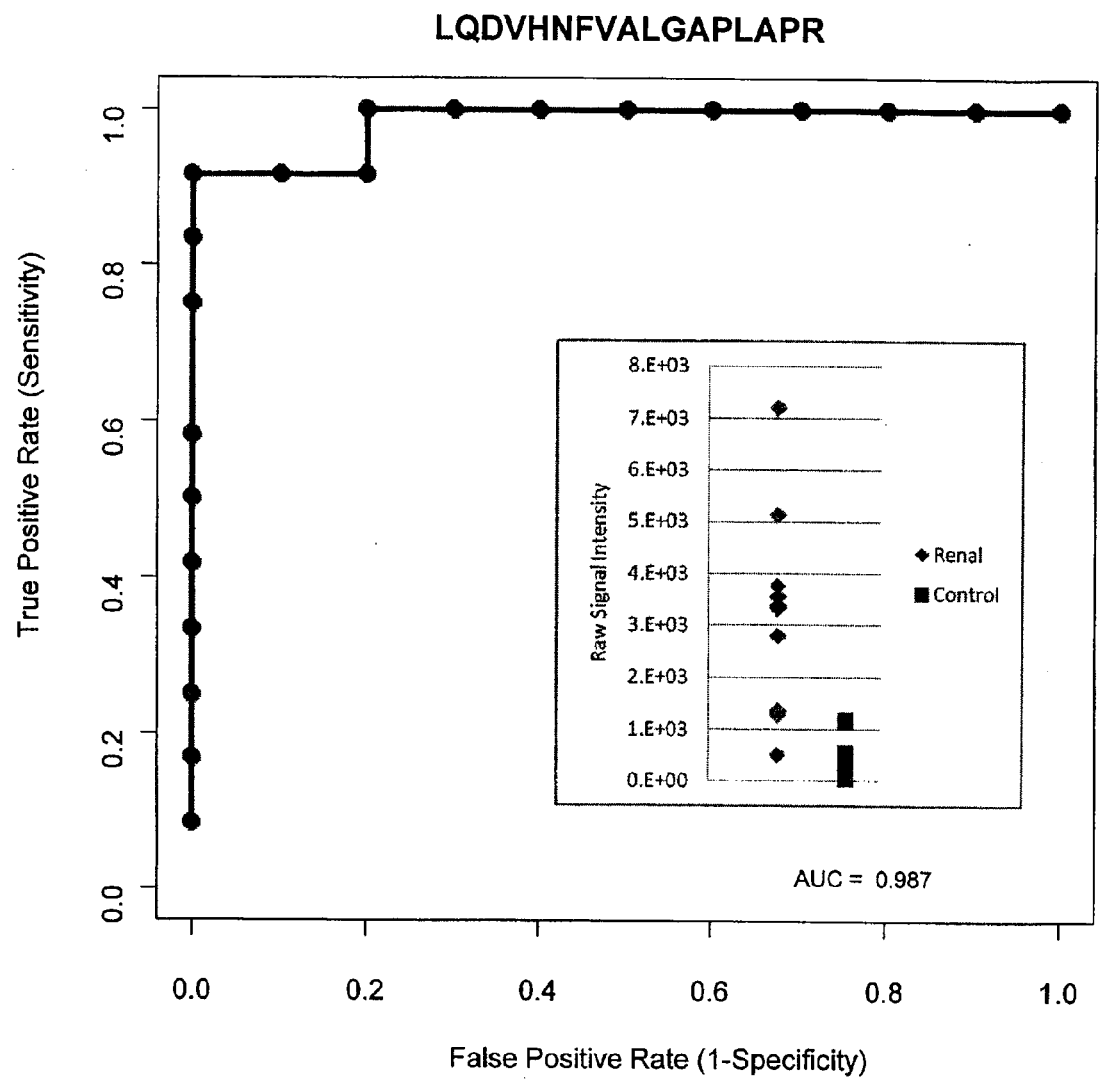
FIGS. 4A-4E are receiver operating characteristic (ROC) curves showing the relationship between sensitivity and 1-selectivity in the diagnosis of renal failure by measurements of various surrogate peptides.
Figure 4B:
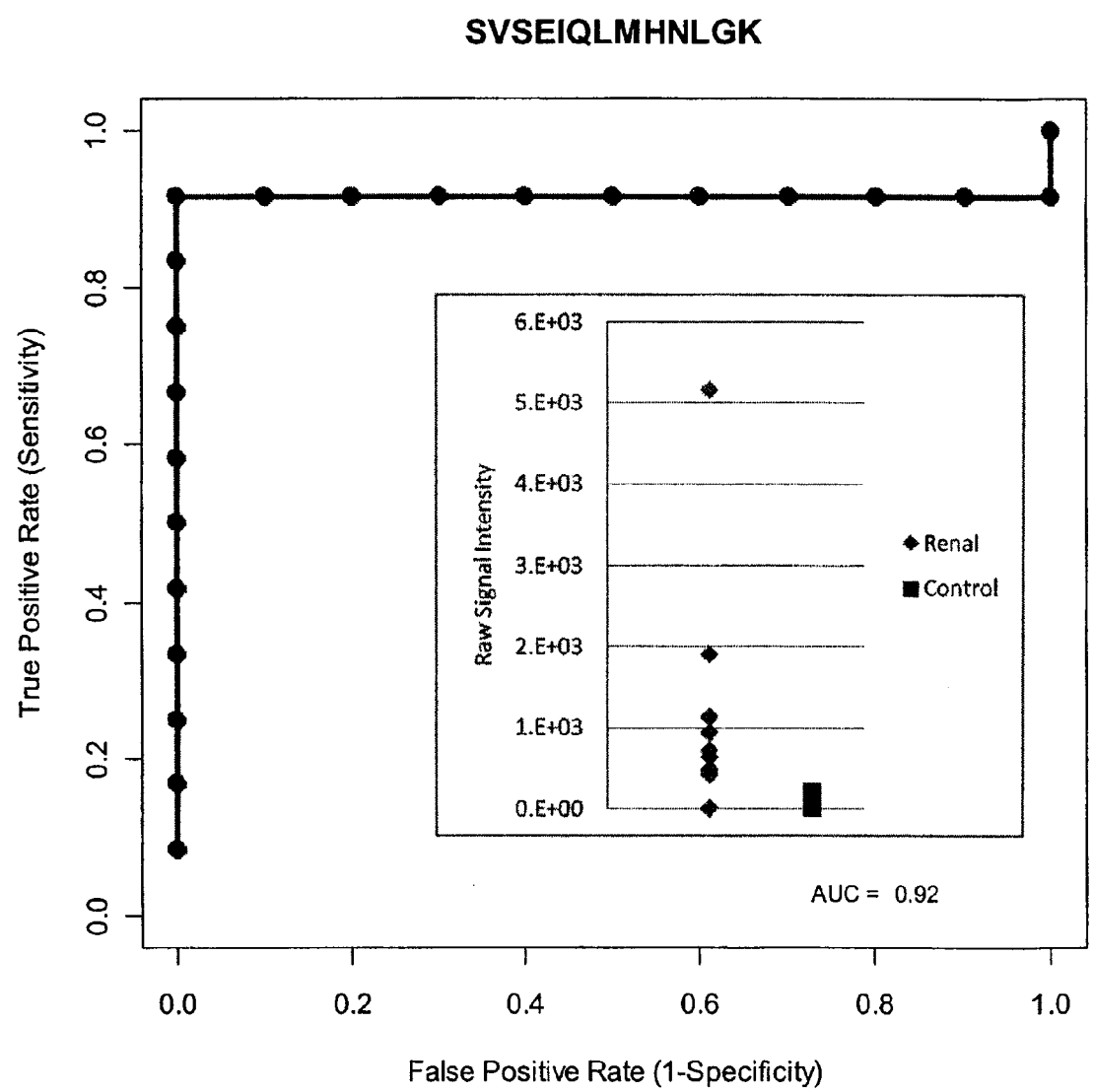
Figure 4C:
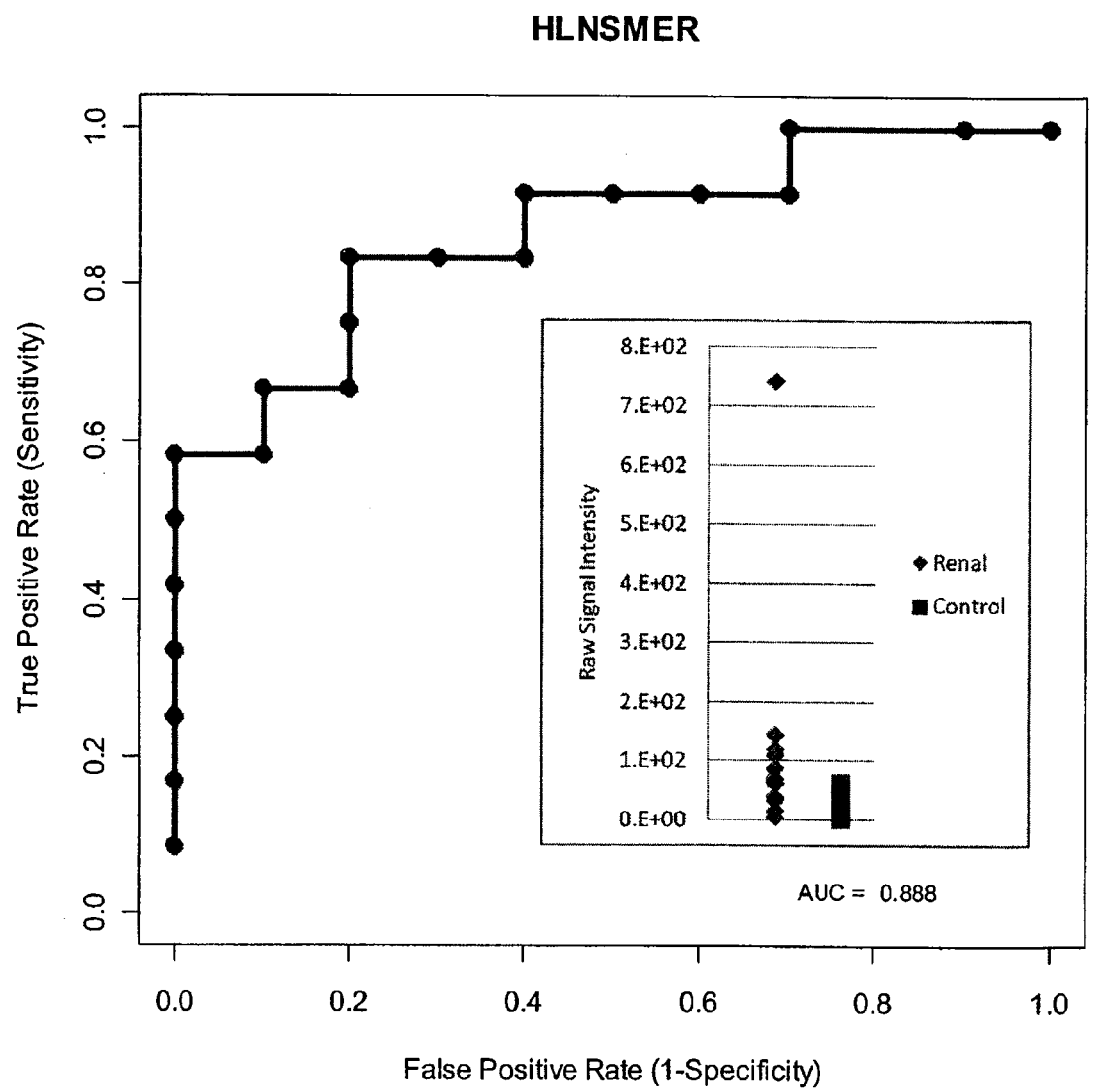
Figure 4D:
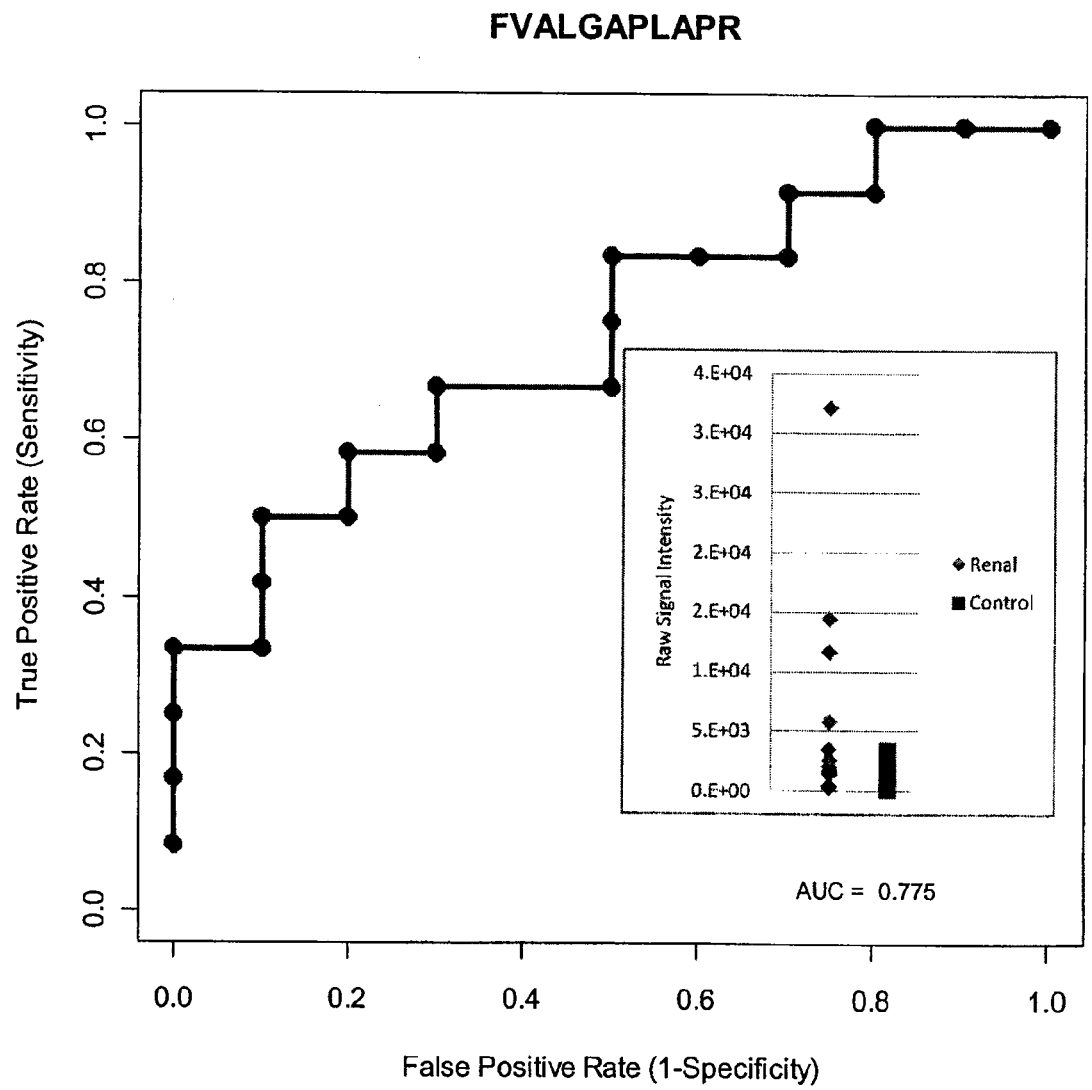
Figure 4E:
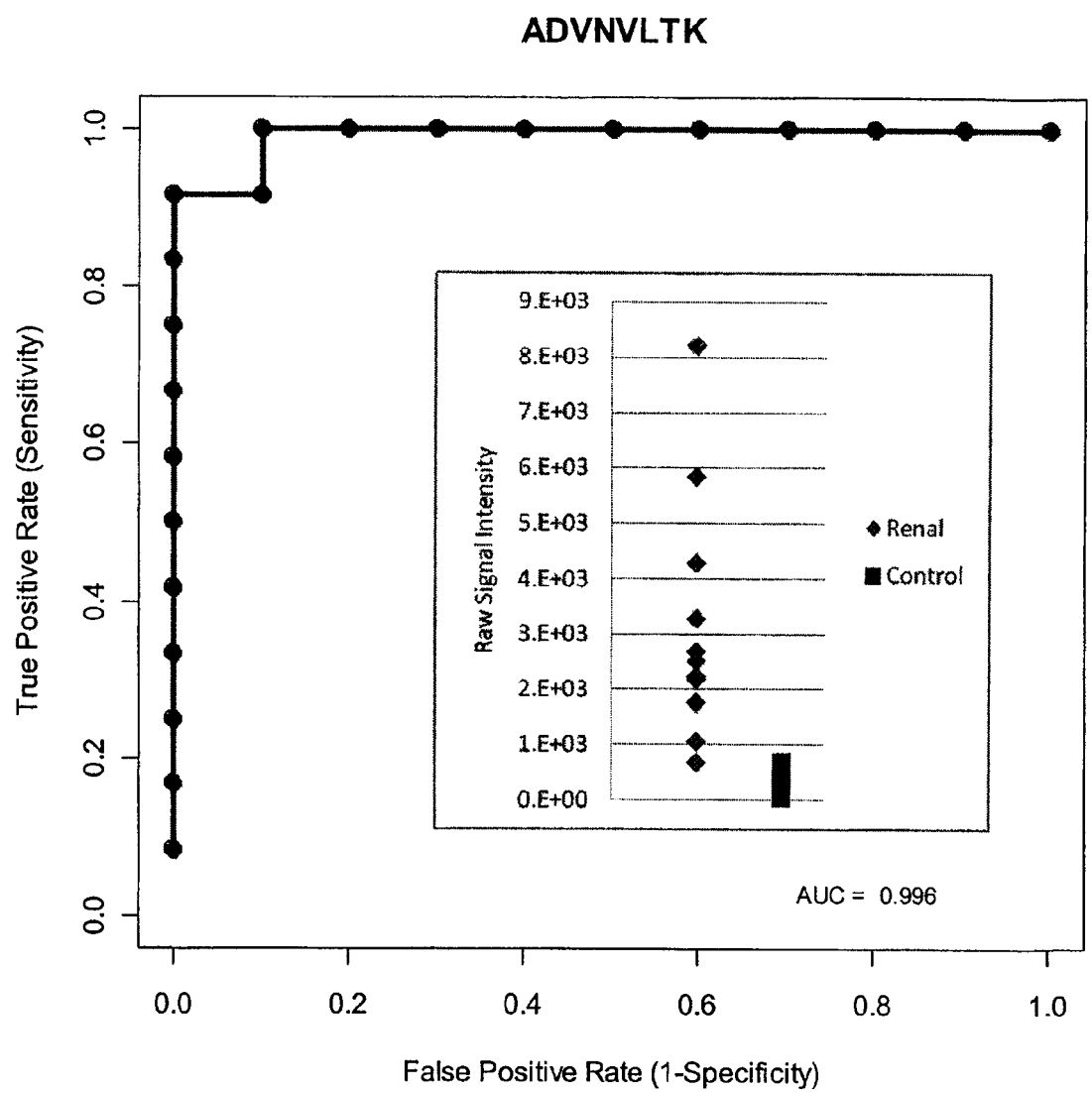

FIGS. 3A and 3B respectively represent Pinpoint screen captures of SRM data for two peptides, SEQ ID NO: 7 and SEQ ID NO: 3 (aa7-13) acquired from replicate normal clinical samples. The topmost panels indicate the peptides and transitions monitored with associated information such as retention time, internal standards and total peak areas. The leftmost bottom panels illustrate the total signal per sample and the center bottom panels illustrate the chromatographic peptide peak shapes and transition ratios for each sample. The rightmost bottom panels illustrate the peak integration areas and individual fragment transitions for both light and heavy peptides.

FIGS. 4A-4E are receiver operating characteristic (ROC) curves constructed from the acquired mass spectrometry data showing the relationship between sensitivity (true positive rate) and 1-specificity (false positive rate) for diagnosis of renal failure based measurement of the amounts of, respectively, the SEQ ID NO: 8, SEQ ID NO: 7, SEQ ID NO: 1, SEQ ID NO: 6 and SEQ ID NO: 5 peptides. Each figure includes as an inset the raw signal intensities for samples in the renal failure group (indicated as diamonds) and control group (indicated as squares), as well as the computed AUC (area under the curve). The degree to which the AUC approaches unity is a measure of the performance of a diagnostic test since it reflects the test performance at all possible cut-off levels. In the present example, the ROC for SEQ ID NO: 8 has an AUC of 0.987, the ROC for SEQ ID NO: 7 has an AUC of 0.92, the ROC of SEQ ID NO: 1 has an AUC of 0.888, the ROC of SEQ ID NO: 6 has an AUC of 0.775, and the ROC of SEQ ID NO: 5 has an AUC of 0.996. These values indicate that each of the aforementioned peptides, and in particular SEQ ID NO: 8, SEQ ID NO: 7 and SEQ ID NO: 5, possess significant diagnostic value in discriminating between normal and renal failure conditions. The data also suggest that diagnostic tests of very high reliability may be conducted using a panel of two or more of the aforementioned peptides.

SEQUENCE LISTING

TABLE I

| Precursor | Product | Sequence | SEQ ID NO | Sequence variant target | Precursor charge state | Ion type |
|---|---|---|---|---|---|---|
| 443.714 | 435.202 | HLNSMER | 1 | | 2 | y3 |
| 296.145 | 435.202 | HLNSMER | 1 | | 3 | y3 |
| 448.718 | 445.21 | HLNSMER[HeavyR] | 1 | | 2 | y3 |
| 299.481 | 445.21 | HLNSMER[HeavyR] | 1 | | 3 | y3 |
| 443.714 | 522.234 | HLNSMER | 1 | | 2 | y4 |
| 296.145 | 522.234 | HLNSMER | 1 | | 3 | y4 |
| 448.718 | 532.242 | HLNSMER[HeavyR] | 1 | | 2 | y4 |
| 299.481 | 532.242 | HLNSMER[HeavyR] | 1 | | 3 | y4 |
| 443.714 | 636.276 | HLNSMER | 1 | | 2 | y5 |
| 296.145 | 636.276 | HLNSMER | 1 | | 3 | y5 |
| 448.718 | 646.285 | HLNSMER[HeavyR] | 1 | | 2 | y5 |
| 299.481 | 646.285 | HLNSMER[HeavyR] | 1 | | 3 | y5 |
| 341.205 | 343.208 | GAPLAPR | 2 | 38-84 | 2 | y3 |
| 341.205 | 456.292 | GAPLAPR | 2 | 38-84 | 2 | y4 |
| 341.205 | 553.345 | GAPLAPR | 2 | | 2 | y5 |
| 406.726 | 317.218 | LMHNLGK | 3 | 3-84 | 2 | y3 |
| 271.486 | 317.218 | LMHNLGK | 3 | 3-84 | 3 | y3 |
| 410.733 | 325.232 | LMHNLGK[HeavyK] | 3 | 3-84 | 2 | y3 |
| 274.158 | 325.232 | LMHNLGK[HeavyK] | 3 | 3-84 | 3 | y3 |
| 406.726 | 431.261 | LMHNLGK | 3 | 3-84 | 2 | y4 |
| 271.486 | 431.261 | LMHNLGK | 3 | 3-84 | 3 | y4 |
| 410.733 | 439.275 | LMHNLGK[HeavyK] | 3 | 3-84 | 2 | y4 |
| 274.158 | 439.275 | LMHNLGK[HeavyK] | 3 | 3-84 | 3 | y4 |
| 406.726 | 568.32 | LMHNLGK | 3 | 3-84 | 2 | y5 |
| 271.486 | 568.32 | LMHNLGK | 3 | 3-84 | 3 | y5 |
| 410.733 | 576.334 | LMHNLGK[HeavyK] | 3 | 3-84 | 2 | y5 |
| 274.158 | 576.334 | LMHNLGK[HeavyK] | 3 | 3-84 | 3 | y5 |
| 397.747 | 343.208 | LGAPLAPR | 4 | 37-84 | 2 | y3 |
| 397.747 | 456.292 | LGAPLAPR | 4 | 37-84 | 2 | y4 |
| 397.747 | 553.345 | LGAPLAPR | 4 | 37-84 | 2 | y5 |
| 397.747 | 624.382 | LGAPLAPR | 4 | 37-84 | 2 | y6 |
| 430.248 | 361.244 | ADVNVLTK | 5 | | 2 | y3 |
| 287.168 | 361.244 | ADVNVLTK | 5 | | 3 | y3 |

TABLE I-continued

| Precursor | Product | Sequence | SEQ ID NO | Sequence variant target | Precursor charge state | Ion type |
|---|---|---|---|---|---|---|
| 434.255 | 369.258 | ADVNVLTK[HeavyK] | 5 | | 2 | y3 |
| 289.839 | 369.258 | ADVNVLTK[HeavyK] | 5 | | 3 | y3 |
| 430.248 | 460.312 | ADVNVLTK | 5 | | 2 | y4 |
| 287.168 | 460.312 | ADVNVLTK | 5 | | 3 | y4 |
| 434.255 | 468.327 | ADVNVLTK[HeavyK] | 5 | | 2 | y4 |
| 289.839 | 468.327 | ADVNVLTK[HeavyK] | 5 | | 3 | y4 |
| 430.248 | 574.355 | ADVNVLTK | 5 | | 2 | y5 |
| 287.168 | 574.355 | ADVNVLTK | 5 | | 3 | y5 |
| 434.255 | 582.37 | ADVNVLTK[HeavyK] | 5 | | 2 | y5 |
| 289.839 | 582.37 | ADVNVLTK[HeavyK] | 5 | | 3 | y5 |
| 430.248 | 673.424 | ADVNVLTK | 5 | | 2 | y6 |
| 287.168 | 673.424 | ADVNVLTK | 5 | | 3 | y6 |
| 434.255 | 681.438 | ADVNVLTK[HeavyK] | 5 | | 2 | y6 |
| 289.839 | 681.438 | ADVNVLTK[HeavyK] | 5 | | 3 | y6 |
| 556.334 | 343.208 | FVALGAPLAPR | 6 | 34-84 | 2 | y3 |
| 556.334 | 456.292 | FVALGAPLAPR | 6 | 34-84 | 2 | y4 |
| 556.334 | 553.345 | FVALGAPLAPR | 6 | 34-84 | 2 | y5 |
| 556.334 | 624.382 | FVALGAPLAPR | 6 | 34-84 | 2 | y6 |
| 556.334 | 681.404 | FVALGAPLAPR | 6 | 34-84 | 2 | y7 |
| 556.334 | 794.488 | FVALGAPLAPR | 6 | 34-84 | 2 | y8 |
| 556.334 | 865.525 | FVALGAPLAPR | 6 | 34-84 | 2 | y9 |
| 728.385 | 317.218 | SVSEIQLMHNLGK | 7 | 1-84 | 2 | y3 |
| 485.926 | 317.218 | SVSEIQLMHNLGK | 7 | 1-84 | 3 | y3 |
| 732.392 | 325.232 | SVSEIQLMHNLGK[HeavyK] | 7 | 1-84 | 2 | y3 |
| 488.597 | 325.232 | SVSEIQLMHNLGK[HeavyK] | 7 | 1-84 | 3 | y3 |
| 728.385 | 431.261 | SVSEIQLMHNLGK | 7 | 1-84 | 2 | y4 |
| 485.926 | 431.261 | SVSEIQLMHNLGK | 7 | 1-84 | 3 | y4 |
| 732.392 | 439.275 | SVSEIQLMHNLGK[HeavyK] | 7 | 1-84 | 2 | y4 |
| 488.597 | 439.275 | SVSEIQLMHNLGK[HeavyK] | 7 | 1-84 | 3 | y4 |
| 728.385 | 568.32 | SVSEIQLMHNLGK | 7 | 1-84 | 2 | y5 |
| 485.926 | 568.32 | SVSEIQLMHNLGK | 7 | 1-84 | 3 | y5 |
| 732.392 | 576.334 | SVSEIQLMHNLGK[HeavyK] | 7 | 1-84 | 2 | y5 |
| 488.597 | 576.334 | SVSEIQLMHNLGK[HeavyK] | 7 | 1-84 | 3 | y5 |
| 728.385 | 699.36 | SVSEIQLMHNLGK | 7 | 1-84 | 2 | y6 |
| 485.926 | 699.36 | SVSEIQLMHNLGK | 7 | 1-84 | 3 | y6 |
| 732.392 | 707.374 | SVSEIQLMHNLGK[HeavyK] | 7 | 1-84 | 2 | y6 |
| 488.597 | 707.374 | SVSEIQLMHNLGK[HeavyK] | 7 | 1-84 | 3 | y6 |
| 728.385 | 812.444 | SVSEIQLMHNLGK | 7 | 1-84 | 2 | y7 |

TABLE I-continued

| Precursor | Product | Sequence | SEQ ID NO | Sequence variant target | Precursor charge state | Ion type |
|---|---|---|---|---|---|---|
| 485.926 | 812.444 | SVSEIQLMHNLGK | 7 | 1-84 | 3 | y7 |
| 732.392 | 820.458 | SVSEIQLMHNLGK[HeavyK] | 7 | 1-84 | 2 | y7 |
| 488.597 | 820.458 | SVSEIQLMHNLGK[HeavyK] | 7 | 1-84 | 3 | y7 |
| 728.385 | 940.503 | SVSEIQLMHNLGK | 7 | 1-84 | 2 | y8 |
| 485.926 | 940.503 | SVSEIQLMHNLGK | 7 | 1-84 | 3 | y8 |
| 732.392 | 948.517 | SVSEIQLMHNLGK[HeavyK] | 7 | 1-84 | 2 | y8 |
| 488.597 | 948.517 | SVSEIQLMHNLGK[HeavyK] | 7 | 1-84 | 3 | y8 |
| 728.385 | 1053.587 | SVSEIQLMHNLGK | 7 | 1-84 | 2 | y9 |
| 485.926 | 1053.587 | SVSEIQLMHNLGK | 7 | 1-84 | 3 | y9 |
| 732.392 | 1061.601 | SVSEIQLMHNLGK[HeavyK] | 7 | 1-84 | 2 | y9 |
| 488.597 | 1061.601 | SVSEIQLMHNLGK[HeavyK] | 7 | 1-84 | 3 | y9 |
| 728.385 | 1182.629 | SVSEIQLMHNLGK | 7 | 1-84 | 2 | y10 |
| 485.926 | 1182.629 | SVSEIQLMHNLGK | 7 | 1-84 | 3 | y10 |
| 732.392 | 1190.64 | SVSEIQLMHNLGK[HeavyK] | 7 | 1-84 | 2 | y10 |
| 488.597 | 1190.644 | SVSEIQLMHNLGK[HeavyK] | 7 | 1-84 | 3 | y10 |
| 728.385 | 1269.661 | SVSEIQLMHNLGK | 7 | 1-84 | 2 | y11 |
| 485.926 | 1269.661 | SVSEIQLMHNLGK | 7 | 1-84 | 3 | y11 |
| 732.392 | 1277.676 | SVSEIQLMHNLGK[HeavyK] | 7 | 1-84 | 2 | y11 |
| 488.597 | 1277.676 | SVSEIQLMHNLGK[HeavyK] | 7 | 1-84 | 3 | y11 |
| 909.505 | 343.208 | LQDVHNFVALGAPLAPR | 8 | | 2 | y3 |
| 606.672 | 343.208 | LQDVHNFVALGAPLAPR | 8 | | 3 | y3 |
| 914.509 | 353.217 | LQDVHNFVALGAPLAPR[HeavyR] | 8 | | 2 | y3 |
| 610.008 | 353.217 | LQDVHNFVALGAPLAPR[HeavyR] | 8 | | 3 | y3 |
| 909.505 | 456.292 | LQDVHNFVALGAPLAPR | 8 | | 2 | y4 |
| 606.672 | 456.292 | LQDVHNFVALGAPLAPR | 8 | | 3 | y4 |
| 914.509 | 466.301 | LQDVHNFVALGAPLAPR[HeavyR] | 8 | | 2 | y4 |
| 610.008 | 466.301 | LQDVHNFVALGAPLAPR[HeavyR] | 8 | | 3 | y4 |
| 909.505 | 553.345 | LQDVHNFVALGAPLAPR | 8 | | 2 | y5 |
| 606.672 | 553.345 | LQDVHNFVALGAPLAPR | 8 | | 3 | y5 |
| 914.509 | 563.353 | LQDVHNFVALGAPLAPR[HeavyR] | 8 | | 2 | y5 |
| 610.008 | 563.353 | LQDVHNFVALGAPLAPR[HeavyR] | 8 | | 3 | y5 |
| 909.505 | 624.382 | LQDVHNFVALGAPLAPR | 8 | | 2 | y6 |
| 606.672 | 624.382 | LQDVHNFVALGAPLAPR | 8 | | 3 | y6 |
| 914.509 | 634.391 | LQDVHNFVALGAPLAPR[HeavyR] | 8 | | 2 | y6 |
| 610.008 | 634.391 | LQDVHNFVALGAPLAPR[HeavyR] | 8 | | 3 | y6 |
| 909.505 | 681.404 | LQDVHNFVALGAPLAPR | 8 | | 2 | y7 |
| 606.672 | 681.404 | LQDVHNFVALGAPLAPR | 8 | | 3 | y7 |
| 914.509 | 691.412 | LQDVHNFVALGAPLAPR[HeavyR] | 8 | | 2 | y7 |

TABLE I-continued

| Precursor | Product | Sequence | SEQ ID NO | Sequence variant target | Precursor charge state | Ion type |
|---|---|---|---|---|---|---|
| 610.008 | 691.412 | LQDVHNFVALGAPLAPR[HeavyR] | 8 | | 3 | y7 |
| 909.505 | 794.488 | LQDVHNFVALGAPLAPR | 8 | | 2 | y8 |
| 606.672 | 794.488 | LQDVHNFVALGAPLAPR | 8 | | 3 | y8 |
| 914.509 | 804.496 | LQDVHNFVALGAPLAPR[HeavyR] | 8 | | 2 | y8 |
| 610.008 | 804.496 | LQDVHNFVALGAPLAPR[HeavyR] | 8 | | 3 | y8 |
| 909.505 | 865.525 | LQDVHNFVALGAPLAPR | 8 | | 2 | y9 |
| 606.672 | 865.525 | LQDVHNFVALGAPLAPR | 8 | | 3 | y9 |
| 914.509 | 875.533 | LQDVHNFVALGAPLAPR[HeavyR] | 8 | | 2 | y9 |
| 610.008 | 875.533 | LQDVHNFVALGAPLAPR[HeavyR] | 8 | | 3 | y9 |
| 909.505 | 964.593 | LQDVHNFVALGAPLAPR | 8 | | 2 | y10 |
| 606.672 | 964.593 | LQDVHNFVALGAPLAPR | 8 | | 3 | y10 |
| 914.509 | 974.602 | LQDVHNFVALGAPLAPR[HeavyR] | 8 | | 2 | y10 |
| 610.008 | 974.602 | LQDVHNFVALGAPLAPR[HeavyR] | 8 | | 3 | y10 |
| 909.505 | 1111.662 | LQDVHNFVALGAPLAPR | 8 | | 2 | y11 |
| 606.672 | 1111.662 | LQDVHNFVALGAPLAPR | 8 | | 3 | y11 |
| 914.509 | 1121.67 | LQDVHNFVALGAPLAPR[HeavyR] | 8 | | 2 | y11 |
| 610.008 | 1121.67 | LQDVHNFVALGAPLAPR[HeavyR] | 8 | | 3 | y11 |
| 909.505 | 1225.705 | LQDVHNFVALGAPLAPR | 8 | | 2 | y12 |
| 606.672 | 1225.705 | LQDVHNFVALGAPLAPR | 8 | | 3 | y12 |
| 914.509 | 1235.713 | LQDVHNFVALGAPLAPR[HeavyR] | 8 | | 2 | y12 |
| 610.008 | 1235.713 | LQDVHNFVALGAPLAPR[HeavyR] | 8 | | 3 | y12 |
| 909.505 | 1362.764 | LQDVHNFVALGAPLAPR | 8 | | 2 | y13 |
| 606.672 | 1362.764 | LQDVHNFVALGAPLAPR | 8 | | 3 | y13 |
| 914.509 | 1372.772 | LQDVHNFVALGAPLAPR[HeavyR] | 8 | | 2 | y13 |
| 610.008 | 1372.772 | LQDVHNFVALGAPLAPR[HeavyR] | 8 | | 3 | y13 |
| 909.505 | 1461.832 | LQDVHNFVALGAPLAPR | 8 | | 2 | y14 |
| 606.672 | 1461.832 | LQDVHNFVALGAPLAPR | 8 | | 3 | y14 |
| 914.509 | 1471.84 | LQDVHNFVALGAPLAPR[HeavyR] | 8 | | 2 | y14 |
| 610.008 | 1471.84 | LQDVHNFVALGAPLAPR[HeavyR] | 8 | | 3 | y14 |

TABLE II

| Precursor | Product | Sequence | SEQ ID NO | Precursor charge state | Ion type | Sequence variant target | aa |
|---|---|---|---|---|---|---|---|
| 486.292 | 635.655 | SVSEIQLMHNLGK | 7 | 3 | y3 | 1-84 | 1-13 |
| 486.292 | 684.469 | SVSEIQLMHNLGK | 7 | 3 | y4 | 1-84 | 1-13 |
| 488.655 | 707.6 | SVSEIQLMHNLGK[HeavyK] | 7 | 3 | y3 | 1-84 | 1-13 |
| 488.655 | 639.456 | SVSEIQLMHNLGK[HeavyK] | 7 | 3 | y4 | 1-84 | 1-13 |

TABLE II-continued

| Precursor | Product | Sequence | SEQ ID NO | Precursor charge state | Ion type | Sequence variant target | aa |
|---|---|---|---|---|---|---|---|
| 406.726 | 317.218 | LMHNLGK | 3 | 2 | y3 | 7-84 | 7-13 |
| 406.726 | 431.261 | LMHNLGK | 3 | 2 | y4 | 7-84 | 7-13 |
| 406.726 | 568.32 | LMHNLGK | 3 | 2 | y5 | 7-84 | 7-13 |
| 410.733 | 325.232 | LMHNLGK[HeavyK] | 3 | 2 | y3 | 7-84 | 7-13 |
| 410.733 | 439.275 | LMHNLGK[HeavyK] | 3 | 2 | y4 | 7-84 | 7-13 |
| 410.733 | 576.334 | LMHNLGK[HeavyK] | 3 | 2 | y5 | 7-84 | 7-13 |
| 443.702 | 636.379 | HLNSMER | 1 | 2 | y3 | Monitoring | 14-20 |
| 443.714 | 619.31 | HLNSMER | 1 | 2 | y5 | Monitoring | 14-20 |
| 443.702 | 749.572 | HLNSMER | 1 | 2 | y4 | Monitoring | 14-20 |
| 448.762 | 646.43 | HLNSMER[HeavyR] | 1 | 2 | y4 | Monitoring | 14-20 |
| 448.762 | 759.501 | HLNSMER[HeavyR] | 1 | 2 | y3 | Monitoring | 14-20 |
| 606.687 | 681.289 | LQDVHNFVALGAPLAPR | 8 | 3 | y3 | Monitoring | 28-44 |
| 606.687 | 553.177 | LQDVHNFVALGAPLAPR | 8 | 3 | y4 | Monitoring | 28-44 |
| 606.687 | 569.259 | LQDVHNFVALGAPLAPR | 8 | 3 | y5 | Monitoring | 28-44 |
| 610.008 | 691.412 | LQDVHNFVALGAPLAPR[HeavyR] | 8 | 3 | y3 | Monitoring | 28-44 |
| 610.008 | 563.353 | LQDVHNFVALGAPLAPR[HeavyR] | 8 | 3 | y4 | Monitoring | 28-44 |
| 610.008 | 569.306 | LQDVHNFVALGAPLAPR[HeavyR] | 8 | 3 | y5 | Monitoring | 28-44 |
| 556.334 | 343.208 | FVALGAPLAPR | 6 | 2 | y3 | 34-84 | 34-44 |
| 556.334 | 456.292 | FVALGAPLAPR | 6 | 2 | y4 | 34-84 | 34-44 |
| 556.334 | 553.345 | FVALGAPLAPR | 6 | 2 | y5 | 34-84 | 34-44 |
| 556.334 | 624.382 | FVALGAPLAPR | 6 | 2 | y6 | 34-84 | 34-44 |
| 556.334 | 681.404 | FVALGAPLAPR | 6 | 2 | y7 | 34-84 | 34-44 |
| 556.334 | 794.488 | FVALGAPLAPR | 6 | 2 | y8 | 34-84 | 34-44 |
| 556.334 | 865.525 | FVALGAPLAPR | 6 | 2 | y9 | 34-84 | 34-44 |
| 430.248 | 337.216 | ADVNVLTK | 5 | 2 | y3 | Monitoring | 73-80 |
| 430.248 | 460.312 | ADVNVLTK | 5 | 2 | y4 | Monitoring | 73-80 |
| 430.248 | 574.355 | ADVNVLTK | 5 | 2 | y5 | Monitoring | 73-80 |
| 430.248 | 673.424 | ADVNVLTK | 5 | 2 | y6 | Monitoring | 73-80 |

What is claimed is:

1. A method for concurrently monitoring parathyroid hormone (PTH) variants in a biological sample, comprising steps of:
    preparing a sample containing PTH peptides from the biological sample, wherein the step of preparing the sample includes purifying and concentrating the PTH variants, proteolytically digesting a portion of the biological sample to produce PTH peptides, and chromatographically separating the sample; and
    subjecting the prepared sample to selective reaction monitoring (SRM) tandem mass spectrometry to concurrently determine the amounts of at least a first and a second PTH peptide, wherein the first PTH peptide is specific to a first PTH variant and the second peptide is specific to a second PTH variant;
    wherein the first PTH variant is intact PTH and the first PTH peptide is SEQ ID NO: 7 (SVSEIQLMHNLGK), and wherein the second PTH variant is a truncated form of PTH selected from a group consisting of PTH (34-84) and PTH (7-84).

2. The method of claim 1, wherein the step of subjecting the prepared sample to SRM tandem mass spectrometry includes monitoring at least two precursor-to-product ion transitions characteristic of the first PTH peptide and at least two precursor-to-product ion transitions characteristic of the second PTH peptide.

3. The method of claim 1, wherein the at least two precursor-to-product ion transitions characteristic of the first PTH peptide are m/z 486→636 and 486→684.

4. The method of claim 1, wherein the second PTH variant is PTH (7-84) and the second PTH peptide is SEQ ID NO: 3 (LMHNLGK).

5. The method of claim 4, wherein the at least two precursor-to-product ion transitions characteristic of the second PTH peptide are selected from the group consisting of m/z 407→317, 407→431, and m/z 407→568.

6. The method of claim 1, wherein the second PTH variant is PTH (34-84), and the second PTH peptide is SEQ ID NO: 6 (FVALGAPLAPR).

7. The method of claim 6, wherein the at least two precursor-to-product ion transitions characteristic of the second PTH peptide are selected from the group consisting of m/z 556→343, 556→456, 556→553, 556→624, m/z 556→681, 556→794 and m/z 556→866.

8. The method of claim 1, wherein the biological sample is one of blood serum and blood plasma.

9. The method of claim 1, wherein the step of preparing the sample includes adding at least one internal reference standard, the reference standard being an isotopically-labeled version of one of the first or second PTH peptide.

* * * * *